United States Patent
Fink (10) Patent No.: US 8,597,242 B2
(45) Date of Patent: Dec. 3, 2013

(54) APPARATUS AND METHOD FOR ESTABLISHING THE PENETRATION DEPTH OF A SLIDING PART OF A MEDICAL HANDPIECE

(75) Inventor: Peter Paul Fink, Holzkirchen (DE)

(73) Assignee: Medi-Globe GmbH, Rohrdorf-Achenmuehle (DE)

( * ) Notice: Subject to any disclaimer, the term of this patent is extended or adjusted under 35 U.S.C. 154(b) by 0 days.

(21) Appl. No.: 13/522,149

(22) PCT Filed: Jan. 29, 2011

(86) PCT No.: PCT/DE2011/000090
§ 371 (c)(1),
(2), (4) Date: Jul. 13, 2012

(87) PCT Pub. No.: WO2011/095156
PCT Pub. Date: Aug. 11, 2011

(65) Prior Publication Data
US 2012/0289901 A1  Nov. 15, 2012

(30) Foreign Application Priority Data

Feb. 2, 2010 (DE) .......................... 10 2010 006 627
Jul. 19, 2010 (DE) .......................... 10 2010 027 578
Aug. 14, 2010 (DE) .......................... 10 2010 034 408

(51) Int. Cl.
*A61M 5/00* (2006.01)
(52) U.S. Cl.
USPC .......................................... 604/117

(58) Field of Classification Search
USPC .......................................... 604/117
See application file for complete search history.

(56) References Cited

U.S. PATENT DOCUMENTS

| 6,976,955 B2 | 12/2005 | Hardin et al. | |
| 8,197,396 B2 * | 6/2012 | Hiraoka | 600/104 |
| 2007/0255311 A1 * | 11/2007 | Hiraoka | 606/205 |
| 2009/0062830 A1 * | 3/2009 | Hiraoka | 606/185 |

FOREIGN PATENT DOCUMENTS

| EP | 1 849 415 | 10/2007 |
| EP | 2 030 574 | 3/2009 |
| JP | 01-113070 | 5/1989 |
| WO | WO 2005/004730 | 1/2005 |

* cited by examiner

*Primary Examiner* — Aarti B Berdichevsky
(74) *Attorney, Agent, or Firm* — Collard & Roe, P.C.

(57) ABSTRACT

A device for establishing the penetration depth of a tubular or rod-shaped sliding part in a receiving part and to a medical handpiece using such devices. There is an adjusting element that surrounds the sliding part and which can be adjusted in the longitudinal direction of the sliding part and can be blocked in the particular position by a clamping device to establish the penetration depth of the sliding part in the receiving part. The clamping device is formed by a rocker element that is arranged between the adjusting element and the sliding part. The rocker element can be moved between a first rotational position, which allows the adjusting element to be slid in the longitudinal direction of the sliding part, and a second rotational position, which blocks the adjusting element from being slid, by rotating the adjusting element transversely to the longitudinal direction of the sliding part.

18 Claims, 3 Drawing Sheets

APPARATUS AND METHOD FOR ESTABLISHING THE PENETRATION DEPTH OF A SLIDING PART OF A MEDICAL HANDPIECE

CROSS REFERENCE TO RELATED APPLICATIONS

This application is the National Stage of PCT/DE2011/000090 filed on Jan. 29, 2011, which claims priority under 35 U.S.C. §119 of German Application No. 10 2010 006 627.3 filed on Feb. 2, 2010, German Application No. 10 2010 027 578.6 filed on Jul. 19, 2010 and German Application No. 10 2010 034 408.7 filed Aug. 14, 2010, the disclosures of which are incorporated by reference. The international application under PCT article 21(2) was not published in English.

The present invention relates to an apparatus for establishing the penetration depth of a tubular or rod-shaped sliding part, particularly of a medical aspiration needle carrier part, in an accommodation part, by means of an adjustment element that surrounds the sliding part, which element is adjustable in the longitudinal direction of the sliding part, and can be locked in the accommodation part, in its position, in each instance, by means of a clamping device, establishing the penetration depth of the sliding part. Furthermore, the present invention relates to a medical handpiece in which a first and a second apparatus of the type stated above are used.

An apparatus of the type stated above is already known (JP 01-113070). In this known apparatus, engagement elements that run in principle in the longitudinal direction of the apparatus and lie opposite one another are assigned to the sliding part that is connected with an aspiration needle and with the adjustment element, which elements are at first not in engagement with one another, when a clamping ring that serves as a clamping device and is displaceable in the longitudinal direction of the apparatus is in a first position. In this first position, a relative displacement of the sliding part, and thus of the aspiration needle relative to the accommodation part that accommodates it, which can be connected with a lumen of an endoscope, is possible. Once the sliding part and therefore the aspiration needle have been pushed into a desired position along the accommodation part, the clamping ring can be displaced into a second position, different from the said first position, in which position the aforementioned engagement elements engage, to a certain extent, so that the sliding part and therefore the aspiration needle can no longer be displaced relative to the said accommodation part.

Fundamentally, in the case of the known device being considered here, single-hand operation is possible, in order to not only achieve a desired adjustment position of the sliding part and thus of the aspiration needle relative to the accommodation part that accommodates it, but also to achieve locking and therefore inhibition of the sliding part in a desired adjustment position with regard to the accommodation part. However, displacement movements in the longitudinal direction of the apparatus must be performed, in each instance, for performing the two functions. As a result, an unintentional and therefore undesirable displacement of the sliding part can come about during displacement of the clamping ring—when the sliding part and thus the aspiration needle are in the desired adjustment position—relative to the accommodation part.

Furthermore, the apparatus effort for implementing the two functions as explained (longitudinal displacement of the sliding part with reference to the accommodation part and locking of the sliding part by means of the clamping ring) is sometimes viewed as being too great. The wish is therefore frequently expressed for an apparatus having a simplified structure as compared with the structure of the related known apparatus.

Furthermore, a handpiece for a medical device is already known (U.S. Pat. No. 6,976,955 B2, WO 2005/004730 A1), consisting of an inner handpiece part carrying two scale divisions, having proximal and distal end parts, which are separated by a delimitation stop that also separates the two scale divisions from one another, a first outer handpiece part that is displaceably disposed on the proximal end part of the inner handpiece part, proximal to the delimitation stop, an elongated sheathing that is affixed to the inner handpiece part and extends axially beyond the distal end and establishes a sheathing lumen, and a fine probe that is affixed to a first outer handpiece part and is displaceably accommodated in the sheathing lumen.

In order to adjust the two outer handpiece parts in desired positions relative to one another with reference to the inner handpiece part, in the case of this known handpiece, and thus to establish the position of the distal end of the fine probe with reference to the distal end of the sheathing that contains it, persons performing this activity can sometimes grasp the inner handpiece part, which carries the two aforementioned scale divisions, with one hand, if the position of one of the outer handpiece parts has not previously been fixed in place by means of a clamping screw. As a result, however, at least a partial region of the scale divisions is covered, thereby making precise positioning of the outer handpiece parts with reference to the said inner handpiece part more difficult.

Furthermore, in the case of the related known handpiece, orientation problems can occur as the result of the arrangement of the outer handpiece parts at opposite end regions of the inner handpiece part, to the effect that effects on the fine probe and the sheathing that accommodates it are connected with the displacement of the outer handpiece part, in each instance, with reference to the said delimitation stop. In the case of the fine probe, a displacement of the outer handpiece part connected with it leads to its distal end moving out when this outer handpiece part is displaced in the direction toward the delimitation stop on the inner handpiece part. For another thing, displacement of the other outer handpiece part connected with the sheathing, in the direction away from the delimitation stop, leads to the distal end of the sheathing moving out. With reference to the delimitation stop of the inner handpiece part in question, two opposite movements of the two outer handpiece parts must therefore be performed, in order to displace the distal ends of the fine probe and the sheathing that accommodates it, in the same direction.

The invention is therefore based on the task of showing a way how an apparatus of the type stated initially and a handpiece using or containing such an apparatus can be implemented in simpler manner than the known apparatus considered initially, and how, in this connection, at the same time, unintentional displacement of the clamping element relative to the accommodation part, after positioning of the sliding part has taken place, can be avoided, at least to a great extent. Furthermore, a way is supposed to be shown how, on the basis of the apparatus in question or by means of the use of a handpiece having two of the apparatuses in question, a handpiece for a medical device can be structured without the problems shown above in connection with the known handpiece, and thus having better manageability as compared with the known handpiece in question. Therefore, on the basis of the apparatus to be created by means of the invention, such a handpiece for a medical device is supposed to be implemented, which can be reliably operated by a person operating it, above all without orientation problems.

The task indicated above is accomplished, in the case of an apparatus of the type stated initially, according to the invention, in that the clamping device is formed in that at least one rocker element is disposed between the adjustment element and the sliding part, which element can be moved, by means of rotating the adjustment element crosswise to the longitudinal direction of the sliding part, between a first rotational position that permits displaceability of the adjustment element in the longitudinal direction of the sliding part, and a second rotational position that inhibits such displaceability, which is different from the first rotational position.

The invention brings with it the advantage that in the apparatus created by it, it is possible to make do with a simpler design principle than the one applied in the known apparatus considered initially. In contrast to the design principle applied for the known apparatus in question, the present invention makes do with at least one rocker element, which can be moved, by means of rotating the adjustment element crosswise to the longitudinal direction of the sliding part, between the first rotational position that permits displaceability of the adjustment element in the longitudinal direction of the sliding part, and the second rotational position that inhibits such displaceability, which is different from the first rotational position.

In the simplest case, in this connection, inhibition of the adjustment element in its desired adjustment position, in each instance, can be achieved by means of utilization of friction between at least one contact surface of the rocker element surrounded by the adjustment element, in each instance, and a contact surface of the sliding part that lies opposite this contact surface. However, as will become evident in greater detail below, other possibilities are also present for actually ensuring the aforementioned inhibition of the adjustment element in its desired adjustment position, in each instance, even more effectively.

The invention furthermore brings with it the advantage that the risk of unintentional displacement of the clamping element after positioning of the sliding part relative to the accommodation part is prevented, at least to a great extent, by means of the combined use of the longitudinal displacement of the sliding part with reference to the accommodation part, and of the rotational movement of the clamping element.

According to a practical further development of the invention, a tooth device is provided on or in the rocker element or on or in the sliding part, for inhibiting the displaceability of the adjustment element along the sliding part, whereby this tooth device lies against the region of the sliding part or of the rocker element that lies opposite it, in the second rotational position of the adjustment element that inhibits displaceability of the adjustment element, or penetrates into this region. As a result, the advantage of a relatively simple inhibition possibility for the displaceability of the adjustment element along the sliding part, which is already sufficiently secure, in many cases, is obtained.

Preferably, the aforementioned adjustment element is formed by an adjustment ring that is shaped, in its inner region that accommodates the rocker element, in oval or sickle shape, in such a manner that the tooth device that is provided on the rocker element and the sliding part lies against the opposite region of the sliding part or of the rocker element, or penetrates into this region, only in the stated second rotational position. This measure brings with it the advantage that a relatively simple inhibition mechanism for secure inhibition of the displaceability of the adjustment element along the sliding part can be achieved.

According to another practical further development of the invention, tooth devices that match one another are provided both on the rocker element and on the sliding part, for inhibiting the displaceability of the adjustment element along the sliding part, which devices inhibit the displaceability of the adjustment element only when they engage into one another, in the stated second rotational position of the adjustment element. In this way, the advantage of a particularly secure inhibition possibility of the displaceability of the adjustment element along the sliding part is obtained.

Preferably, the aforementioned adjustment element is formed by an adjustment ring that is shaped, in its inner region that accommodates the rocker element, in oval or sickle shape, in such a manner that the tooth devices that match one another on the rocker element and the sliding part are brought into engagement with one another only in the stated second rotational position and inhibit the displaceability of the adjustment element. This measure contributes to an additional increase in the advantage that in this way, a relatively simple inhibition mechanism for secure inhibition of the displaceability of the adjustment element along the sliding part can be achieved.

Preferably, the adjustment ring has at least one projecting rib part on its inside, which part permits limiting the angle of rotation of the adjustment ring on the sliding part by means of making contact with the tooth segment part. As a result, the advantage of relatively simple guidance of the adjustment ring on the sliding part is obtained.

It is practical if the angle of rotation extends, in the case of two rib parts that lie at least approximately opposite one another, to a value of about 180° minus the angle width over which the rocker element or the rocker element, in each instance, extends. As a result, the advantage of secure guidance of the adjustment ring on the sliding part is obtained.

According to another practical further development of the invention, the adjustment ring carries at least one, preferably three activation cams on its outside. As a result, the advantage of very simple operability of the adjustment ring on the sliding part is obtained.

It is practical if the activation cam, in each instance, projects radially from the adjustment ring. This brings with it the advantage of particularly simple operability of the adjustment ring on the sliding part.

According to other practical further developments of the invention, the rocker element, in each instance, is guided so as to prevent rotation in the longitudinal direction of the sliding part. Here, preventing rotation means guidance with reference to the sliding part. In this way, the advantage of stable and securely positioned displaceability of the rocker element, in each instance, in the longitudinal direction of the accommodation part, and therefore also securing of the previously considered adjustment and displacement function of the sliding part with reference to the accommodation part, is obtained.

According to yet other particularly practical further developments of the invention, its apparatus is provided in duplicate to form a medical handpiece for a medical device, namely as a first apparatus and as a second apparatus, comprising the following characteristics:

the first apparatus permits establishing the penetration depth of a first tubular sliding part in a first accommodation part, and the second apparatus permits establishing the penetration depth of a second tubular sliding part in a second accommodation part;

the first apparatus and the second apparatus are disposed one behind the other, in such a manner that the first sliding part of the first apparatus is configured at least in part as the second accommodation part for the second sliding part of the second apparatus;

the first sliding part and the second sliding part are surrounded, in each instance, by an adjustment element, relative to which the related sliding part, in each instance, is displaceable;

the first adjustment element and the second adjustment element can be inhibited in their position, in each instance, by means of a separate clamping device, establishing the penetration depth of the related first or second sliding part in the first or second accommodation part, respectively, that accommodates it;

each clamping device is formed in that at least one rocker element is disposed between the adjustment element, in each instance, and its related sliding part, which element can be moved, by means of rotating the adjustment element in question crosswise to the longitudinal direction of the related sliding part, between a first rotational position that permits displaceability of the sliding part in the longitudinal direction relative to the related adjustment element, and a second rotational position that inhibits such displaceability, which is different from the first rotational position;

elements of the medical device are connected with the first accommodation part and the second sliding part.

In this way, the advantage is achieved that by means of the combined use of two apparatuses according to the invention, a simple handpiece for a medical device, which can be securely handled, can be made available, in connection with which no irritations for the handling personnel occur during the course of the adjustment procedures.

According to a practical further development of the invention, the medical device is formed in that a medical hollow or aspiration needle is connected with the first accommodation part, which needle extends in the longitudinal direction through the first accommodation part, the first sliding part with the second accommodation part configured on it, and the second sliding part, and that a sheathing that surrounds the medical hollow or aspiration needle is connected with the second sliding part. In this manner, a medical device as it is particularly required for endoscopic work on individuals, which consists of a medical hollow or aspiration needle and a sheathing that surrounds the former in displaceable manner can be made available, in advantageous manner.

Preferably, an end connection element, particularly a screw connection element for a connection with the medical hollow or aspiration needle, is disposed at the proximal end region of the first accommodation part. In this way, the hollow or aspiration needle can be affixed to the handpiece in interchangeable manner, in advantageous manner, something that is particularly important if different hollow or aspiration needles are used during a work procedure.

It is particularly advantageous, according to another practical embodiment of the invention, that the first sliding part and the second sliding part contain one or more markings or scale divisions, in each instance. In this way, precise and precisely repeatable adjustments of the sliding parts with reference to the related adjustment elements can be undertaken, in particularly simple manner.

According to another practical embodiment of the invention, a connection element, particularly a screw connection element, is provided at the distal end region of the second sliding part, for affixing it to a counter-connection element of another medical device, particularly a work channel of an endoscope. This brings with it the advantage that the handpiece can be connected, in simple and secure manner, for work with other medical devices, and particularly with work channels of endoscopes.

Preferably, a connector connection element, particularly a screw connection element, is disposed at the proximal end region of the first accommodation part, if applicable for affixing a further medical device. This measure also contributes to being able to connect the handpiece in simple and secure manner, for work with other medical devices, such as with a syringe or a suction device or a flushing device.

It is practical if the first accommodation part is structured as a handle part. This facilitates manageability of the handpiece during adjustment of the two sliding parts.

It is very particularly advantageous to structure the part of the first sliding part that is configured as the second accommodation part for the second sliding part of the second apparatus as a handle part. In this way, extremely advantageous manageability of the handpiece during adjustment of the two sliding parts is obtained; during these adjustments, the sliding parts are not touched by hand by the person undertaking the adjustments in question.

The invention will be explained in greater detail below, using exemplary embodiments, using drawings.

The Drawings Show

Before the drawings are discussed further, it should be noted that the same or corresponding devices or elements are referred to with the same or corresponding reference symbols in all the drawings.

Figure 1:
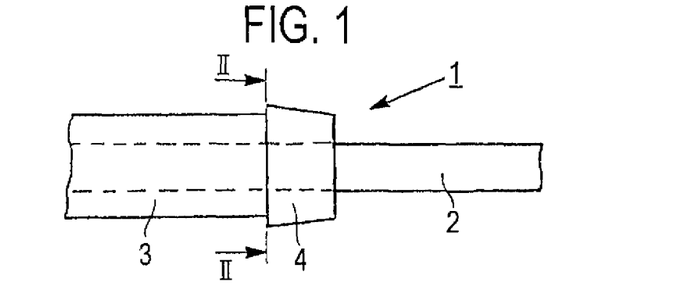
FIG. 1 a schematic top view of an apparatus according to an embodiment of the invention, in a size that can be different from the size used in practice.

In FIG. 1, an apparatus 1 according to an embodiment of the invention is shown in a schematic top view. The apparatus 1 serves for establishing the penetration or immersion depth of a tubular or rod-shaped sliding part 2 in an accommodation part 3, by means of an adjustment element 4 that surrounds the sliding part 2. The accommodation part 3 has an opening, not designated in greater detail here, for displaceable accommodation of the sliding part 2; it itself can be configured in tubular manner, for example. In the present case, the sliding part 2 has a circular cross-section, which—as will still become evident—is interrupted by grooves that run in a straight line in the longitudinal direction of the sliding part 2. The sliding part 2, the accommodation part 3, and the adjustment element 4 can consist of plastic, in each instance.

The adjustment element 4 is fundamentally adjustable in the longitudinal direction of the sliding part 2, and can be inhibited in its position, in each instance, by means of a clamping device 5, which cannot be seen in FIG. 1 but will still be considered in greater detail below, using FIGS. 2 and 3, establishing the penetration or immersion depth of the sliding part 2 in the accommodation part 3.

At this point, it should also be noted that the apparatus 1 in FIG. 1 is shown in a size that can be different from an apparatus used in practice. Thus, the apparatus 1 in question, for example in connection with accommodation of a medical aspiration needle carrier part that forms the sliding part 2, can have transverse dimensions or diameters that are half as great as those that are evident from FIG. 1. In this case, the aspiration needle carrier part can serve to accommodate the needle of an injection syringe at its proximal end (lying on the right in FIG. 1), and the accommodation part 3, which accommodates the sliding part 2 with an aspiration needle affixed at its distal end (lying on the left in FIG. 1), can be connected with a lumen of an endoscope (not shown), for example by means of a Luer lock connection.

Figure 2:
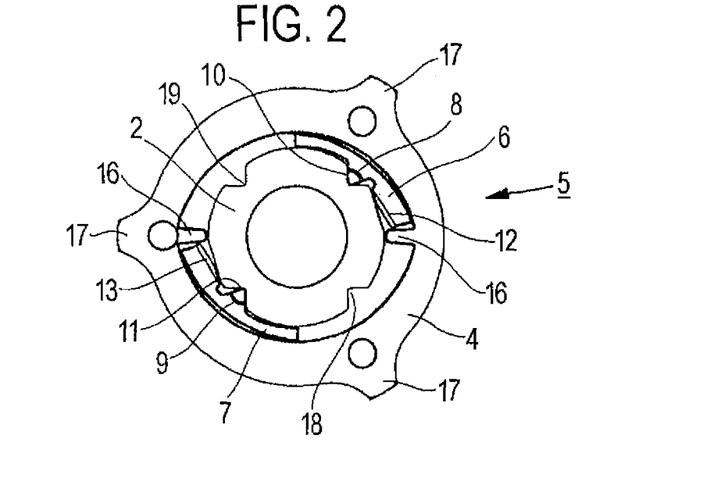
FIG. 2 a side view, enlarged with reference to the representation in FIG. 1, of the apparatus in question, according to a sectional plane II-II entered in FIG. 1, whereby the apparatus is illustrated with an adjustment element that is situated in a first rotational position.
Figure 3:
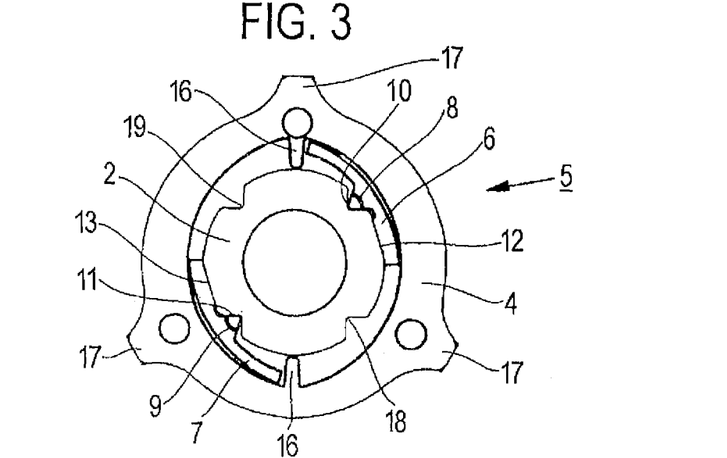
FIG. 3 a side view, enlarged with reference to the representation in FIG. 1, of the apparatus in question, according to a sectional plane II-II entered in FIG. 1, whereby the apparatus is illustrated with an adjustment element that is situated in a second rotational position.

In FIGS. 2 and 3, the aforementioned clamping device 5 is illustrated in greater detail, in terms of its structure. The two FIGS. 2 and 3 show the apparatus 1, in a greatly enlarged side view, in each instance, in accordance with the direction of the arrow of the sectional plane II-II entered in FIG. 1, in other words in the region of the adjustment element 4 that surrounds the sliding part 2, with which this adjustment element 4 is enabled to lie against a contact surface of the accommodation part 3. The adjustment element 4 has an opening region that is shaped with oval symmetry in the present case. The opening region in question has two regions that lie relatively close to one another, and two regions that lie relatively far apart from one another, between the former.

As is evident from FIGS. 2 and 3, the clamping device 5, in the present case, surrounds two rocker elements 6 and 7 that are disposed between the adjustment element 4 and the sliding part 2, which elements can be moved, by means of rotating the adjustment element 4 crosswise to its longitudinal direction, between a first rotational position that permits displaceability of the adjustment element 4 in the longitudinal direction of the sliding part 2 (FIG. 2), and a second rotational position that inhibits such displaceability (FIG. 3), which is different from the first rotational position. It should be noted here that according to the invention, it is fundamentally possible to make do with at least one rocker element corresponding to the rocker elements 6 and 7. However, the use of two or more rocker elements placed symmetrically around the sliding part 2 brings with it the advantage of simpler and problem-free rotatability of the adjustment element 4. The rocker element, in each instance, can consist of plastic or a metal.

As can be seen from FIGS. 2 and 3, the two rocker elements 6 and 7 have a sickle-shaped cross-section in the longitudinal direction of the apparatus 1. In its central regions that lie on the inside, the rocker elements 6 and 7 are provided with bearing journals 8 and 9, respectively, which are accommodated by bearing grooves 10 and 11, respectively, in the outer circumference of the sliding part 2, in such a manner that the rocker elements 6 and 7 can be tilted about these bearing grooves 10 and 11. In this connection, the rocker element 6, 7, in each instance, is guided in the sliding part 2 so as to prevent rotation in the longitudinal direction of the accommodation part 3.

In its one regions, which border on the bearing journals 8 and 9 of the rocker elements 6 and 7, the rocker elements are provided with contact regions 12 and 13, respectively, that are configured to be thickened toward the outer circumference side of the sliding part 2, in FIGS. 2 and 3. With these contact regions 12 and 13, the rocker elements 6 and 7 can be brought into contact, by means of rotation of the adjustment element 4, with the outer circumference surface of the latter. In this connection, the contact regions 12 and 13 in question can act as brake wedges, in each instance, with their surfaces that face the sliding part 2, specifically either with their normal metal surface or with a brake lining applied to this surface. In this way, the sliding part 2 can be inhibited in its displaceability into the accommodation part 3.

Figure 4:
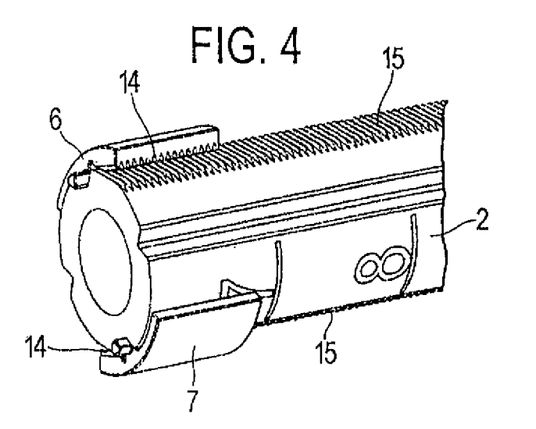
FIG. 4 a detail, in a perspective representation, of an apparatus according to another embodiment of the invention, with an adjustment element of this apparatus situated in a first rotational position.
Figure 5:
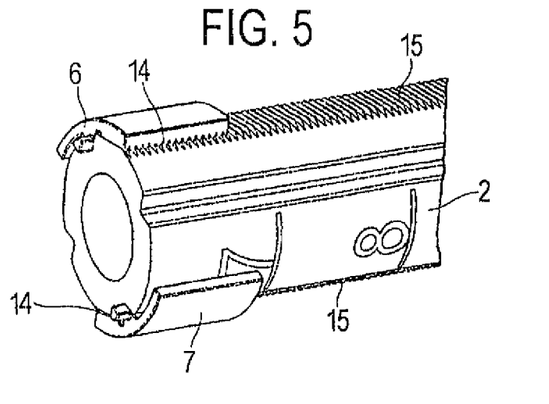
FIG. 5 a detail, in a perspective representation, of the apparatus according to FIG. 4, with an adjustment element of this apparatus situated in a second rotational position.

In deviation from the configuration and use of the contact regions 12 and 13 as explained above, for inhibiting the displaceability of the sliding part 2 into the accommodation part 3 (establishing the penetration depth), as an alternative, it is also possible to proceed in such a manner that a tooth device 14 or 15 is provided on the rocker element 6 or 7 or on the sliding part 2, as is illustrated in FIGS. 4 and 5. This tooth device lies against the region of the sliding part 2 or the rocker element 6 or 7 that lies opposite it in the second rotational position of the adjustment element 4 that inhibits displaceability of the adjustment element 4, or penetrates into this region. In this case, the tooth device 14 or 15 will preferably consist of a relatively hard material, such as metal, and the region on which the tooth device in question is to be brought into contact or into which the tooth device penetrates will preferably consist of a relatively soft material, such as plastic.

Supplementally, it should still be noted, with regard to the alternative mentioned above, with regard to the representation of FIGS. 2 and 3, that there, the adjustment element 4 is formed by an adjustment ring 4 that is shaped in oval or sickle shape, in its inner region that accommodates the rocker element 6 or 7, in such a manner that the tooth device 14 or 15 provided on the rocker element 6 or 7 or on the sliding part 2 lies against the region of the sliding part or of the rocker element that lies opposite it only in its said second rotational position, or penetrates into this region.

In a further development of the configuration of the rocker element 6 or 7 or of the sliding part 2, in each instance, as last considered, for inhibiting the displaceability of the sliding part 2 into the accommodation part 3, tooth devices 14 and 15 that match one another can be provided both on the rocker element 6, 7, in each instance, and on the sliding part 2; these devices inhibit the displaceability of the adjustment element 4 only when they engage into one another in the aforementioned second rotational position of the latter. The two tooth devices 14 and 15 are illustrated in a perspective representation, in each instance, together with the rocker elements 6 and 7 and a partial section of the sliding part 2, in FIGS. 4 and 5. In this connection, the sliding part 2 is provided, over its length, with a scale division, which, in connection with the adjustment element or ring 4 left out in FIGS. 4 and 5, makes precise and easily repeatable establishment of the penetration depth of the sliding part 2 in the accommodation part 3 possible. In this connection, the right outside of the adjustment element or ring 4 that surrounds the rocker elements 6 and 7, using the view of FIGS. 4 and 5 as a basis, can be used as a measurement edge for the aforementioned scale division. In this connection, the tooth device 14 is situated on the underside of the thickened region of the rocker elements 6, 7, in each instance, and here it extends over the entire width of the underside. The tooth device 15 extends, on the top and the underside of the sliding part 2, over that length over which this sliding part 2 is supposed to be displaceable in the accommodation part 3 shown in FIG. 1, for example over its entire length. The tooth device 14 can consist, for example, of a hard plastic or of metal, and the tooth device 15 can consist of a hard plastic.

From FIG. 4, in this connection the state in which the two tooth devices 14 and 15 are not in engagement with one another can be seen. In this state, the sliding part 2 can easily be displaced in the accommodation part 3 shown in FIG. 1. In this connection, the rocker parts 6 and 7 slide in the bearing grooves 10 and 11, respectively, of the sliding part 2 without hindrance, with their bearing journals 8 and 9, respectively (see, in this regard, FIGS. 2 and 3).

From FIG. 5, the state in which the two tooth devices 14 and 15 are in engagement with one another can be seen. In this state, the sliding part 2 can no longer be displaced into the accommodation part 3 shown in FIG. 1, or displaced out of it. The rocker parts 6 and 7 inhibit such displaceability and thereby establish the penetration depth of the sliding part 2 in the accommodation part 3.

Supplementally, it should still be noted, making reference to the representations of FIGS. 2 and 3, that the adjustment element 4 is formed by an adjustment ring 4 that is shaped in sickle shape, in its inner region that accommodates the rocker element 6 or 7, in such a manner that the tooth devices 14, 15 provided on the rocker element 6, 7 and on the sliding part 2 are brought into engagement with one another only in the second rotational position already mentioned, and thereby inhibit displaceability of the adjustment element 4.

The aforementioned adjustment ring 4 has at least one—in the present case, in view of the symmetrical structure of the inside of the adjustment ring 4—two projecting rib parts 16, which permit limiting the angle of rotation of the adjustment ring 4 on the sliding part 2 by means of contact on the rocker part 6 or 7, in each instance. This is evident from a comparison of the representations in FIGS. 2 and 3. The related angle of rotation amounts to about 180° in the case of two rib parts 16 that lie at least approximately opposite one another, minus the angle width over which the rocker part 6 or 7, in each instance, extends.

The adjustment ring 4 has at least one, but preferably—as is evident from FIGS. 2 and 3—three activation cams 17, which project radially away from the adjustment ring 4, in each instance, here, and which allow easy operability of this adjustment ring 4 and thus secure one-hand operation of the entire apparatus 1, with regard to establishing the penetration depth of the sliding part 2 in the accommodation part 3. However, this one-hand operation of the apparatus 1 is fundamentally made possible even without the activation cams 17.

In addition to the bearing grooves 10 and 11 mentioned above, the sliding part 2 furthermore has grooves 18, 19 that run in the longitudinal direction of the sliding part 2, but these grooves extend only over a limited length of the sliding part 2. Pin elements (not shown) work together with these grooves 18, 19, which lie diametrically opposite one another and furthermore run symmetrical to the bearing grooves 10 and 11, which elements are contained in or on the accommodation part 3. By means of engagement of these pin elements into the grooves 18, 19, and by means of the displaceability of the sliding part 2 in the accommodation part 3 only over the aforementioned limited length, it is ensured that the sliding part 2 cannot be unintentionally pushed completely into the accommodation part 3 and pulled out of it again: the sliding part 2 is connected with the accommodation part 3 in essentially undetachable manner.

Furthermore, it should also be noted that the invention is not restricted to the embodiments explained using the drawings. Thus, for example, the functions of adjustment ring 4 and sliding part 2 can be exchanged, in accordance with a kinematic reversal. This means that in the case of such an alternative, the adjustment ring 4 can no longer be rotated, and that then, the sliding part 2, with the rocker element 6, 7, in each instance, can also be rotated about its longitudinal axis, in addition to its longitudinal displaceability. In this case, the inside of the adjustment ring 4 considered using FIGS. 2 and 3 can possess a circular shape, and the sliding part 2 can be provided with an oval cross-section. In this connection, it can be appropriate to firmly connect the adjustment ring 4 with the accommodation part 3.

In deviation from the embodiments explained above, the present invention fundamentally makes do with one rocker element between the sliding part 2 and the adjustment element 4. In this case, the inside shape of the adjustment element 4 does not need to be shaped with oval symmetry. Instead, a single sickle-shaped configuration of a part of the opening of the adjustment element 4 is sufficient.

While round cross-sections have been assumed, in the embodiments explained above, not only for the sliding part 2 but also for the opening of the accommodation part 3 that surrounds this sliding part 2, other cross-sections can also be provided, such as, for example, quadragonal or, in general, polygonal cross-sectional shapes.

The tooth devices 14, 15 can also be structured differently from what is evident in FIGS. 4 and 5. Thus, for example, the tooth device 14 does not need to extend over the entire width of the rocker element 6 or 7, in each instance. Fundamentally, it is possible to make do with only one tooth element in/on the rocker element 6 or 7, in each instance, and with a plurality of tooth element accommodations in/on the sliding part 2 or the rocker part 6 or 7, in each instance.

Using FIGS. 6 and 7, it will be explained below how the design principles evident from FIGS. 1 to 5 come into practical use in the case of a medical handpiece 20 for a medical device. It will be shown how apparatuses according to the invention are used in practice, in the case of a medical handpiece.

Figure 6:
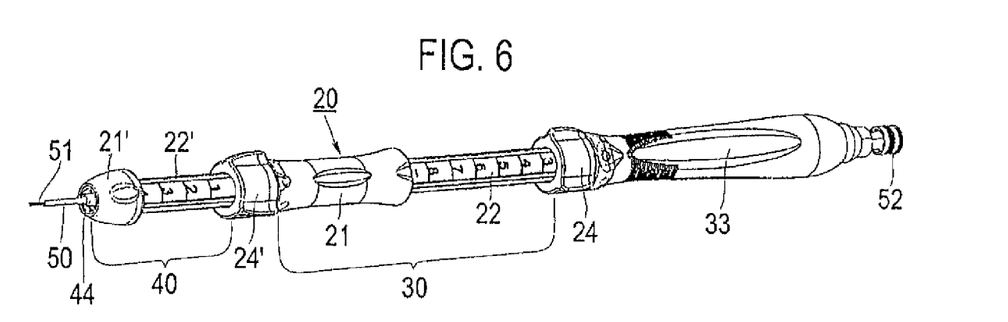
FIG. 6 on a scale not to scale, a perspective view of a handpiece containing two apparatuses according to the invention, corresponding to an embodiment of the invention, and FIG. 7 on a scale not to scale, an exploded view of the handpiece shown in FIG. 6.

In FIG. 6, the handpiece 20 is shown according to an embodiment of the invention for a medical device, in a pulled-apart state, ready for work. In the present exemplary embodiment, this medical device is a medical hollow needle or aspiration needle 51, which is surrounded by a sheathing 50 and is displaceable in the latter. The sheathing 50 in question is also displaceable on the hollow needle or aspiration needle 51, as will still become evident below; it can be configured in spiral shape at least at its distal end—that is the end shown on the left in FIG. 6. The hollow or aspiration needle 51 in question is connected, in the present case, with a first accommodation part or proximal handle part 33 with its proximal end. Its proximal end is furthermore connected with a proximal end part 52 to which another medical device can be connected in the present exemplary embodiment, such as, for example, a syringe or a suction device or a flushing device. However, the proximal end part 52 in question can also be a screw closure part that can be screwed onto a counter-screw part provided at the proximal end of the handpiece. In the present embodiment of the handpiece 20 according to the invention, this screw closure part is connected with the proximal end of the medical hollow needle or aspiration needle 51.

It should be noted at this point that the aforementioned medical device can also be formed by other medical apparatuses, such as a collection or clamping apparatus or by a cutting apparatus, such as tongs or scissors, specifically accommodated by a sheathing that corresponds to the sheathing 50, in each instance, and displaceable relative to the latter.

The handpiece 20 comprises two apparatuses according to the invention. According to a first view, the one of these two apparatuses—specifically when looking at the handpiece 20 from its proximal end—that is the end shown on the right in FIG. 6—comprises a first sliding part 30 and the first accommodation part or proximal handle part 33 already mentioned, into which the first sliding part 30 can be pushed and from which it can be pulled out. The other of the two apparatuses according to the invention comprises, in this view, a second sliding part 40 that is accommodated by the first sliding part 30 that is configured and acts as an accommodation part for this sliding part 40, and can be pushed into this part and pulled out of it.

Corresponding to a second view, the one of these two apparatuses—specifically looking at the handpiece 20 from its distal end—this is the end shown on the left in FIG. 6—comprises the sliding part 40 and the accommodation part or handle part 30 that accommodates it, into which the said sliding part 40 can be pushed and from which it can be pulled out. In this view, the other of the two apparatuses according to the invention comprises the accommodation part or handle part 30 that acts as a sliding part, which part is accommodated by the proximal handle part 33 and can be pushed into the latter and pulled out of it.

The two views explained above have shown that the proximal handle part 33, the sliding part 30, and the sliding part 40 represent a telescope-type structure, in each instance, in which the sliding part 40 is displaceably accommodated by the sliding part 30, and in which the sliding part 30 is displaceably accommodated by the proximal handle part 33.

Now that the structure of the handpiece 20 has been explained in general, with regard to the two apparatuses according to the invention used there, making reference to FIG. 6, the more detailed structure of these two apparatuses will now be discussed, referring to the first views explained above.

According to FIG. 6, the first sliding part 30 consists of a second accommodation part or central handle part 21, and a first sliding tube 22. This sliding tube 22 contains a scale division, in the present case; however, if applicable, it can also have only one marking or multiple markings or multiple scale divisions. In the position evident from FIG. 6, the sliding tube 22 is firmly connected with the second accommodation part or central handle part 21, for example by means of a glued connection.

A first adjustment element or rotational element 24 is provided on the sliding tube 22, according to FIG. 6, which element is adjustable along the sliding tube 22 or which, alternatively, is affixed to the proximal handle part 33 in rotatable manner, and can be rotated about the sliding tube 22. By means of rotating this adjustment element or rotational element 24 between a first rotational position and a second rotational position, different from the former, the displaceability of the sliding tube 22 and thereby of the first sliding part 30 in the proximal handle part 33 can be released or inhibited, and thereby the penetration depth of the sliding tube 22 in the proximal handle part 33 can be established.

The second sliding part 40 consists of a second sliding tube 22' and a head part 21' affixed at its distal end. The sliding tube 22' and the head part 21' can be firmly connected with one another, for example by means of a glued connection. In the present case, the sliding tube 22' contains a scale division; however, it can also have only one marking or multiple markings, or multiple scale divisions. The sliding tube 22' can be pushed into the second accommodation part or central handle part 21 and pulled out of it, in order to establish its penetration depth in this part.

To establish the penetration depth, in each instance, of the sliding tube 22' in the second accommodation part or central handle part 21, a second adjustment element or rotational element 24' is provided on the sliding tube 22, according to FIG. 6, which element is affixed on the distal end region of the second accommodation part or central handle part 21, so as to rotate. By means of rotation of this adjustment element or rotational element 24' between a first rotational position and a second rotational position, different from the former, the displaceability of the sliding tube 22' and thus of the second sliding part 40 in the first sliding part 30 can be released or inhibited, and thus the penetration depth of the sliding tube 22' in the second accommodation part or central handle part 21 of the first sliding part 30 can be established.

In FIG. 6, a screw part 44 is shown on the head part 21' affixed to the distal end of the handpiece 20; this part is, in particular, a screw connection element for affixation to a counter-connection element of a medical device, particularly a work channel of an endoscope. This screw connection element can be a Luer lock connection element, which can be connected with a corresponding counterpart Luer lock connection element.

Now that the structure of the handpiece 20 in the pulled-apart state has been explained, using FIG. 6, its pushed-together state will be briefly discussed. In the pushed-together state of the handpiece 20, the distal end region of the second accommodation part or central handle part 21 lies against the proximal end region of the first adjustment element or rotational element 24, and the proximal end region of the second adjustment element or rotational element 24' lies against the distal end region of the head part 21'. The first sliding tube 22 is pushed completely into the first accommodation part 33 of the handpiece 20, and the second sliding tube 22' is pushed completely into the second accommodation part 21 of the handpiece 20.

Now, reference will be made to FIG. 7, in which the handpiece shown in FIG. 6 is illustrated in an exploded view, in order to explain the assembly of the individual elements of the handpiece 20 as examples.

Figure 7:
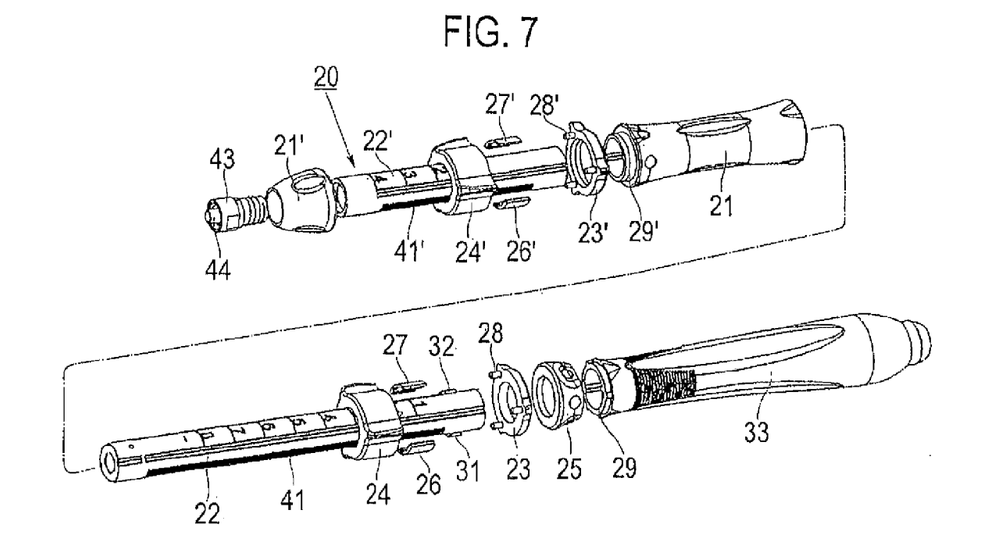

In the lower part of the exploded view according to FIG. 7, the first sliding tube 22 is shown, on which the first adjustment element or rotational element 24 can be rotated between two rotational positions, and is accommodated in the longitudinal direction of the sliding tube 24 in displaceable manner. Along the first sliding tube 24, in FIG. 7, a tooth device 41 of at least two tooth devices that extend at least approximately diametrically on the outside of the sliding tube 24 is indicated. These tooth devices represent rod-like elements, in the tooth mechanisms of which a first rocker element 26 or a second rocker element 27 can be brought into engagement with at least one tooth, in each instance, by means of rotating the adjustment element or rotational element 24, or released from such engagement.

The two rocker elements 26 and 27 are situated, after the handpiece 20 has been assembled, between the first sliding tube 22 and an oval accommodation opening in the adjustment element or rotational element 24. By means of the configuration of the adjustment element or rotational element 24 in its interior, with the oval accommodation opening, it is possible, as has been explained in connection with FIGS. 1 to 5, to release the two rocker elements 26 and 27 with their tooth mechanisms from the aforementioned tooth devices, such as the tooth device 41, in a first rotational position of the first adjustment element or rotational element 24, in other words to bring them out of engagement, and to bring them into engagement in a second rotational position, different from this first rotational position.

For centered affixation of the first adjustment element or rotational element 24 on the first sliding tube 22, a first clamping or adjustment ring 23 having at least one, in the present case three pins projecting from its side that faces the adjustment element or rotational element 24, is affixed on the adjustment element or rotational element 24 in question; these pins can be accommodated by corresponding accommodation openings that are situated in the first adjustment element or rotational element 24. One of these pins is designated with 28 in FIG. 7.

As was mentioned in connection with FIG. 6, the first sliding tube 22, together with the second accommodation part or central handle part 21, forms the first sliding part 30. For this purpose, the first sliding part 22 is firmly affixed to the accommodation part or central handle part 21 with its distal end, shown on the left in FIG. 7, for example in a corresponding accommodation opening of the accommodation part or central handle part 21 and/or by means of gluing it on.

The first sliding part 30 can be pushed into a longitudinal opening that passes through the first accommodation part or proximal handle part 33, with its sliding tube 22, and can be pulled out of it. In order to ensure, during this extraction, that the sliding tube 22 is not pulled completely out of the accommodation part or proximal handle part 33, an inhibition mechanism is provided. This inhibition mechanism comprises, according to FIG. 7, an accommodation ring 25 for accommodating the sliding tube 22, and two delimitation beads 31, 32 that project radially away from the circumference of the sliding tube 22, which can be formed, if applicable, by an arc-shaped clamp that projects away from the outer surface of the sliding tube 22. The accommodation ring 25 serves for insertion into an accommodation element or hole 29 at the distal end of the proximal handle part 33. Before the accommodation ring 25 is inserted into the accommodation element or hole 29 and attached in it, however, the sliding tube 22 must be pushed through the accommodation ring 25 with its distal end. In this manner, the delimitation beads 31, 32 that project radially away from the sliding tube 22 are then accommodated in the accommodation opening of the proximal handle part 33 after assembly of the handpiece 20. Because the delimitation beads 31, 32 act as stops on the accommodation ring 25, the sliding tube 22 can no longer be pulled completely out of the handle part 33.

In the following, the part of the handpiece 20 shown in the upper part of the exploded view according to FIG. 7 will be considered in greater detail. In this part, the accommodation part or central handle part 21 that belongs to the first sliding part 30 is shown on the right side. This accommodation part or central handle part 21 is provided, at its distal end, with an accommodation element 29' on which a second clamping or adjustment ring 23', corresponding to the first clamping or adjustment ring 23, can be set so as to rotate, for example by means of an engagement connection. The adjustment ring 23' in turn is firmly connected with a second adjustment element or rotational element 24' that corresponds to the first adjustment element or rotational element 24, for example by means of a glued connection. Pins that project from the distal side of the adjustment ring 23' serve for precise alignment of the adjustment ring 23' on the second adjustment element or rotational element 24'; one of these is indicated with 28', and they are accommodated by corresponding accommodation holes in the adjustment element or rotational element 24'.

Before the aforementioned connection between the adjustment element or rotational element 24' and the adjustment ring 23' is produced, however, third and fourth rocker elements 26', 27' that correspond to the first and second rocker element 26, 27 must be inserted into the interstice between a second sliding tube 22' and the interior of the adjustment element or rotational element 24' that surrounds this tube. The rocker elements 26', 27' in question are provided, like the rocker elements 26 and 27 already considered, with a tooth structure that comprises at least one tooth element, in each instance, on their sides that face the sliding tube 22', which structure can be accommodated by a rack-like tooth device that extends along the sliding tube 22', on its outside. In FIG. 7, one of the two rack-like tooth devices provided on the sliding tube 22' is designated with 41'.

The aforementioned tooth structure of the two rocker elements 26', 27' is brought out of engagement with the related rack-like tooth device of the sliding tube 22' in a first rotational position of the adjustment element or rotational element 24'. In this rotational position, the sliding tube 22' is thereby released for longitudinal displacement, so that it can then be displaced, in its longitudinal direction, with reference to the second accommodation part or central handle part 21. In a second rotational position of the adjustment element or rotational element 24', different from the first rotational position, the two rocker elements 26', 27' are brought into engagement, with their tooth structures, with the related rack-like tooth devices of the sliding tube 22'. In this second rotational position, the sliding tube 22' can no longer be displaced with reference to the second accommodation part or central handle part 21; its penetration depth in the second accommodation part or central handle part 21 has thereby been established. By means of this displacement, the extension length of the sheathing 50 connected with the sliding tube 22' can be adjusted and thereby established at the distal end of the handpiece 20, relative to the extension length of the medical device connected with the first accommodation part or proximal handle part 33, such as the hollow or aspiration needle 51.

In order to bring about clamping and release of the sliding tube 22', the adjustment element or rotational element 24', like the adjustment element or rotational element 24, has an oval cross-section in its interior, which brings the two rocker elements 26', 27', with their tooth structures, into engagement with the related rack-like tooth devices of the sliding tube 22' in its first rotational position, and into engagement in the second rotational position.

So that the sliding tube 22' is prevented from being pulled out completely from the handle part 21 after assembly of the handpiece 20, an inhibition mechanism is also provided in the proximal end region of the sliding tube 22'. This inhibition mechanism can be implemented in corresponding manner as explained in connection with the sliding tube 22. However, it is also possible here to have the third and fourth rocker elements 26' and 27' accommodated in guide grooves of the sliding tube 22' with their bearing journals, as was illustrated in greater detail in FIGS. 1 to 5. These guide grooves end at a fixed distance of about 10 mm, for example, in front of the proximal end of the sliding tube 22', and thereby exert a stop function on the rocker elements 26' and 27' and consequently on the entire adjustment element or rotational element 24'.

At this point, it should be noted that an inhibition mechanism corresponding to the inhibition mechanism comprising the third and fourth rocker elements 26' and 27' can also be provided in connection with the first and second rocker elements 26 and 27.

The head part 21' must be connected with the distal end of the sliding tube 22', specifically preferably in fixed manner, for example by means of a glued connection. Finally, a distal connector part 43 must still be inserted into the head part 21', for example by means of a screw connection and/or glued connection. The screw part 44 already mentioned in connection with FIG. 6, with which the handpiece 20 can be screwed onto a corresponding counter-screw part that can be provided in the entry region of a work channel of an endoscope, for example, is contained in this distal connector part 43.

In the case of the handpiece 20 according to the present invention, explained above using an exemplary embodiment, two apparatuses 1 according to the invention are therefore used in combination, in order to adjust the penetration depth of a tubular sliding part, in each instance, in an accommodation part, by means of an adjustment element that surrounds the sliding part, in each instance. Here, the one or first apparatus comprises the first accommodation part or proximal handle part 33 and the first sliding part 30. Here, the other or second apparatus comprises the second accommodation part or central handle part 21 of the first sliding part 30 just mentioned, and the second sliding tube 22' of the second sliding part 40.

Because a medical device, such as, in particular, a hollow or aspiration needle 51, is connected with the first accommodation part or proximal handle part 33 in the case of the handpiece 20 as explained, and because a sheathing 50 that surrounds the medical device in question, such as the aforementioned hollow or aspiration needle 51, is connected with the second sliding tube 22' of the second sliding part 40 provided at the distal end of the handpiece 20, the following adjustments can be made:

1. By means of establishing the penetration depth of the first sliding part 30 in the first accommodation part or proximal handle part 33, for one thing the extension length of the part of the medical device, such as the aforementioned hollow or aspiration needle 51, guided out from the distal end of the handpiece 20, can be established.
2. By means of establishing the penetration depth of the second sliding tube 22' of the second sliding part 40 in the second accommodation part or central handle part 21 of the first sliding part 30, for another thing, the extension length of the part of the medical device, such as the sheathing 50 surrounding the aforementioned hollow or aspiration needle 51, guided out from the distal end of the handpiece 20, can be established.

These two adjustment procedures as just explained are required for performing medical work as it is carried out, in particular, by means of endoscopes in individuals. Because the first sliding part 30 has the second accommodation part or central handle part 21, the handpiece 20 using apparatuses according to the invention can be handled better when adjusting the extension length of the sheathing 50 than the known handpiece for a medical device considered initially; specifically, when the handpiece 20 is held for adjusting the penetration depth of the second sliding tube 22' into the second accommodation part or central handle part 21, no marking region or scale region of the two sliding tubes 22 and 22' is covered. Because similar displacements of the two sliding tubes 22 and 22' also lead to similar displacements of the aspiration needle 51 and its sheathing 50, no orientation problems occur for the operating personnel of the handpiece 20 in question.

Reference Symbol List
1 apparatus
2 sliding part
3 accommodation part
4 adjustment element, adjustment ring
5 clamping device
6 rocker element
7 rocker element
8 bearing journal
9 bearing journal
10 bearing groove
11 bearing groove
12 contact region
13 contact region
14 tooth device
15 tooth device
16 rib parts
17 activation cam
18 groove
19 groove
20 handpiece
21 second accommodation part or central handle part
21' head part
22 first sliding tube
22' second sliding tube
23 first clamping or adjustment ring
23' second clamping or adjustment ring
24 first adjustment element or rotation element
24' second adjustment element or rotation element
25 accommodation ring
26 first rocker element
26' second rocker element
27 third rocker element
27' fourth rocker element
28 pin
28' pin
29 accommodation element
29' accommodation element
30 first sliding part
31 delimitation bead
32 delimitation bead
33 first accommodation part or proximal handle part
40 second sliding part
41 tooth device
41' tooth device
43 distal connection part
44 connection element
50 sheathing
51 medical hollow or aspiration needle
52 proximal connection part

The invention claimed is:

1. Apparatus (1) for establishing the penetration depth of a tubular or rod-shaped sliding part (2), particularly of a medical aspiration needle carrier part, in an accommodation part (3), by means of an adjustment element (4) that surrounds the sliding part (2), which element is adjustable in the longitudinal direction of the sliding part (2), and can be locked in the accommodation part (3), in its position, in each instance, by means of a clamping device (5), establishing the penetration depth of the sliding part (2), wherein the clamping device (5) is formed in that at least one rocker element (6; 7) is disposed between the adjustment element (4) and the sliding part (2), which element can be moved, by means of rotating the adjustment element (4) crosswise to the longitudinal direction of the sliding part (2), between a first rotational position that permits displaceability of the adjustment element (4) in the longitudinal direction of the sliding part (2), and a second rotational position that inhibits such displaceability, which is different from the first rotational position.

2. Apparatus according to claim 1. wherein the rocker element (6, 7), in each instance, is guided so as to prevent rotation in the longitudinal direction of the sliding part (2).

3. Apparatus according to claim 1, wherein tooth devices (14, 15) that match one another are provided both on the rocker element (6; 7) and on the sliding part (2), for inhibiting the displaceability of the adjustment element (4) along the sliding part (2), which devices inhibit the displaceability of the adjustment element (4) only when they engage into one another, in the stated second rotational position of the adjustment element (4).

4. Apparatus according to claim 3, wherein the adjustment element (4) is formed by an adjustment ring (4) that is shaped, in its inner region that accommodates the rocker element (6; 7), in oval or sickle shape, in such a manner that the tooth devices (14, 15) that match one another on the rocker element (6; 7) and the sliding part (2) arc brought into engagement with one another only in the stated second rotational position and inhibit the displaceability of the adjustment element (4).

5. Apparatus according to claim 1, characterized in that wherein a tooth device (14 or 15) is provided on the rocker element (6; 7) or on the sliding part (2), for inhibiting the displaceability of the adjustment element (4) along the sliding part (2), and that this tooth device (14 or 15) lies against the region of the sliding part (2) or of the rocker element (6; 7) that lies opposite it, in the second rotational position of the adjustment element (4) that inhibits displaceability of the adjustment element (4), or penetrates into this region.

6. Apparatus according to claim 5, wherein the adjustment element (4) is formed by an adjustment ring (4) that is shaped, in its inner region that accommodates the rocker element (6; 7), in oval or sickle shape, in such a manner that the tooth device (14 or 15) provided on the rocker element (6; 7) or on the sliding part (2) lies against the opposite region of the sliding part (2) or of the rocker element (6; 7) only in the stated second rotational position, or penetrates into this region.

7. Apparatus according to claim 6, wherein the adjustment ring (4) has at least one projecting rib part (16) on its inside, which part permits limiting the angle of rotation of the adjustment ring (4) on the sliding part (2) by means of making contact with the rocker element (6; 7).

8. Apparatus according to claim 7, characterized in that wherein the angle of rotation, in the case of two rib parts (16) that lie at least approximately opposite one another, has a value of about 180° minus the angle width over which the rocker element (6; 7), in each instance, extends.

9. Apparatus according to claim 6, wherein the adjustment ring (4) carries at leas*: one, preferably three activation cams (17) on its outside.

10. Apparatus according to claim 9, wherein the activation cam (17), in each instance, projects radially from the adjustment ring (4).

11. Medical handpiece (20) for a medical device, using a first and a second apparatus according to claim 1, wherein the first apparatus permits establishing the penetration depth of a first tubular sliding part (30; 21, 22) in a first accommodation part (33), and wherein the second apparatus permits establishing the penetration depth of a second tubular sliding part (40; 21', 22') in a second accommodation part (21), comprising the following characteristics:

the first apparatus and the second apparatus are disposed one behind the other, in such a manner that the first sliding part (30; 21, 22) of the first apparatus is configured at least in part as the second accommodation part (21) for the second sliding part (40; 21' 22') of the second apparatus;

the first sliding part (30; 21, 22) and the second sliding part (40; 21', 22') are surrounded, in each instance, by an adjustment element (24; 24'), relative to which the related sliding part (30; 21, 22; 40; 21', 22'), in each instance, is displaceable;

the first adjustment element (24) and the second adjustment element (24') can be inhibited in their position, in each instance, by moans of a separate clamping device, establishing the penetration depth of the related first or second sliding part (30; 21, 22; 40; 21', 22') in the first or second accommodation part (33; 21), respectively, that accommodates it;

each clamping device is formed in that at least one rocker element (26, 27; 26', 21') is disposed between the adjustment element (24; 24'), in each instance, and its related sliding part (30; 21, 22; 40; 21', 22'), which element car. be moved, by moans of rotating the adjustment element (24, 24') in question crosswise to the longitudinal direction of the related sliding part (30; 21, 22; 40; 21', 22'), between a first rotational position that permits displaceability of the sliding part (30; 21, 22; 40; 21', 22') in the longitudinal direction relative to the related adjustment element (24; 24'), and a second rotational position that inhibits such displaceability, which is different from the first rotational position;

elements (50, 51) of the medical device are connected with the first accommodation part (33) and the second sliding part (40; 21', 22').

12. Handpiece according to claim 11, wherein the first sliding part (30; 21, 22) and the second sliding part (40; 21', 22') contain one or more markings or scale divisions, in each instance.

13. Handpiece according to claim 11, wherein a connection element (44), particularly a screw connection element, is provided at the distal end region of the second sliding part (40; 21', 22'), for affixing it to a counter-connection element of another medical device, particularly a work channel of an endoscope.

14. Handpiece according to claim 11, wherein a connector connection element (52), particularly a screw connection element, is disposed at the proximal end region of the first accommodation part (33), if applicable for affixing a further medical device.

15. Handpiece according to claim 11. wherein the first accommodation part (33) is structured as a handle part (33).

16. Handpiece according to claim 11, wherein the part of the first sliding part (30; 21, 22) that is configured as the second accommodation part (21) for the second sliding part (40; 21', 22') of the second apparatus is structured as a handle part (21).

17. Handpiece according to claim 11, wherein the medical device is formed in that a medical hollow or aspiration needle (51) is connected with the first accommodation part (33), which needle extends in the longitudinal direction through the first accommodation part (33), the first sliding part (30; 21, 22) with the second accommodation part (21) configured on it, and the second sliding part (40; 21', 22'), and that a sheathing (50) that surrounds the medical hollow or aspiration needle (51) is connected with the second sliding part (40; 21', 22').

18. Handpiece according to claim 17, wherein an end connection element, particularly a screw connection element (52) for a connection with the medical hollow or aspiration needle (51), is disposed at the proximal end region of the first sliding part (30; 21, 22).

* * * * *